(12) United States Patent  
David

(10) Patent No.: US 7,648,522 B2
(45) Date of Patent: Jan. 19, 2010

(54) BONE FIXATION ASSEMBLY AND METHOD

(75) Inventor: Jérôme David, Bordeaux (FR)

(73) Assignee: Stryker Spine (FR)

( * ) Notice: Subject to any disclaimer, the term of this patent is extended or adjusted under 35 U.S.C. 154(b) by 274 days.

(21) Appl. No.: 10/695,849

(22) Filed: Oct. 29, 2003

(65) Prior Publication Data
US 2005/0070901 A1 Mar. 31, 2005

(30) Foreign Application Priority Data
Sep. 26, 2003 (FR) ................... 03 11291

(51) Int. Cl.
A61B 17/70 (2006.01)
(52) U.S. Cl. ................ 606/266; 606/252; 606/328
(58) Field of Classification Search ............ 606/61, 606/72, 73, 246, 250–253, 260, 266, 267, 606/270, 278, 300, 305, 319, 264, 279, 328, 606/60; 403/76, 90; 74/617; 81/132; 269/76
See application file for complete search history.

(56) References Cited

U.S. PATENT DOCUMENTS

| 196,564 | A | * | 10/1877 | Curtis ................ 403/69 |
|---|---|---|---|---|
| 3,375,044 | A | * | 3/1968 | Peterson .............. 403/77 |
| 4,484,570 | A | * | 11/1984 | Sutter et al. ........... 606/282 |
| 5,176,680 | A | | 1/1993 | Vignaud et al. |
| 5,190,543 | A | | 3/1993 | Schlapfer |
| 5,312,404 | A | | 5/1994 | Asher et al. |
| 5,474,551 | A | | 12/1995 | Finn et al. |
| 5,501,684 | A | | 3/1996 | Schlapfer et al. |
| 5,520,689 | A | | 5/1996 | Schlapfer et al. |
| 5,527,314 | A | * | 6/1996 | Brumfield et al. ........ 606/278 |
| 5,534,002 | A | | 7/1996 | Brumfield et al. |
| 5,613,968 | A | | 3/1997 | Lin |
| 5,628,740 | A | * | 5/1997 | Mullane ............... 606/61 |
| 5,643,259 | A | | 7/1997 | Sasso et al. |
| 5,643,263 | A | * | 7/1997 | Simonson ............. 606/61 |
| 5,702,394 | A | | 12/1997 | Henry et al. |
| 5,776,135 | A | * | 7/1998 | Errico et al. ........... 606/61 |
| 5,814,046 | A | | 9/1998 | Hopf |
| 5,938,663 | A | | 8/1999 | Petreto |
| 5,947,967 | A | | 9/1999 | Barker |
| 6,050,997 | A | * | 4/2000 | Mullane ............... 606/61 |
| 6,080,156 | A | | 6/2000 | Asher et al. |
| 6,123,706 | A | * | 9/2000 | Lange ................ 606/61 |
| 6,146,383 | A | * | 11/2000 | Studer et al. ........... 606/61 |
| 6,187,005 | B1 | | 2/2001 | Brace et al. |
| 6,231,575 | B1 | | 5/2001 | Krag |

(Continued)

FOREIGN PATENT DOCUMENTS

EP 0 933 065 A 8/1999

(Continued)

Primary Examiner—Thomas C Barrett
Assistant Examiner—James L. Swiger
(74) Attorney, Agent, or Firm—Lerner, David, Littenberg, Krumholz & Mentlik, LLP

(57) ABSTRACT

A bone fixation assembly and method of fixing bones including a fixation element having a head portion, a unitary coupling element and at least one locking element. The unitary coupling element includes a first bore adapted to slidably receive the head portion of the fixation element. A first locking element is adapted to secure the head portion in the first bore.

40 Claims, 6 Drawing Sheets

U.S. PATENT DOCUMENTS

| | | | |
|---|---|---|---|
| 6,280,443 B1 * | 8/2001 | Gu et al. | 606/61 |
| 6,471,703 B1 | 10/2002 | Ashman | |
| 6,482,207 B1 | 11/2002 | Errico | |
| 6,623,485 B2 * | 9/2003 | Doubler et al. | 606/61 |
| 6,626,906 B1 * | 9/2003 | Young | 606/61 |
| 6,660,005 B2 | 12/2003 | Toyama et al. | |
| 6,685,705 B1 * | 2/2004 | Taylor | 606/278 |
| 6,709,434 B1 * | 3/2004 | Gournay et al. | 606/266 |
| 6,755,830 B2 * | 6/2004 | Minfelde et al. | 606/61 |
| 2002/0082601 A1 | 6/2002 | Toyama et al. | |
| 2002/0143341 A1 | 10/2002 | Biedermann et al. | |
| 2002/0169450 A1 | 11/2002 | Lange | |
| 2003/0028191 A1 * | 2/2003 | Shluzas | 606/61 |
| 2003/0045878 A1 | 3/2003 | Petit et al. | |
| 2003/0055426 A1 | 3/2003 | Carbone et al. | |
| 2006/0058787 A1 | 3/2006 | David | |

FOREIGN PATENT DOCUMENTS

| | | |
|---|---|---|
| EP | 1 254 640 | 11/2002 |
| FR | 2 781 663 | 2/2000 |
| WO | WO-02/34151 | 5/2002 |

* cited by examiner

BONE FIXATION ASSEMBLY AND METHOD

CROSS-REFERENCE TO RELATED APPLICATIONS

The present application claims priority of French Application No. 0311291 filed on Sep. 26, 2003, the contents of which are hereby incorporated by reference in their entirety.

FIELD OF THE INVENTION

The invention relates to bone fixation devices, and in particular, to pedicle fixation assemblies and methods used in spinal fixation procedures.

BACKGROUND OF THE INVENTION

The spinal column is a highly complex system of bones and connective tissues that provides support for the body and protects the delicate spinal cord and nerves. The spinal column includes a series of stacked vertebral bodies, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord and nerves is located behind the vertebral bodies.

A surgical technique commonly referred to as spinal fixation uses surgical implants for fusing together and/or mechanically immobilizing two or more vertebral bodies of the spinal column. Spinal fixation may also be used to alter the alignment of adjacent vertebral bodies relative to one another to change the overall alignment of the spinal column. Such techniques have been used effectively to treat a wide variety of conditions and, in most cases, to relieve pain.

One spinal fixation technique involves immobilizing the spine using orthopedic stabilizing rods, commonly referred to as spine rods, which run generally parallel to the spine. This technique involves exposing the spine posteriorly and fastening bone screws to the pedicles of vertebral bodies. The pedicle screws are generally placed at least one per vertebra and serve as anchor points for the spine rods. Clamping elements adapted for receiving a spine rod therethrough are then used to join the spine rods to the pedicle screws. The aligning influence of the spine rods forces the spinal column to conform to a more desirable shape. In certain instances, the spine rods may be bent to achieve the desired curvature of the spinal column.

Most existing rod fixation systems require several components to build the systems. Each additional component or instrument required to assemble the fixation system adds to the complexity of the surgical technique. A need has thus arisen for improved fixation systems that minimize the assembly of small pieces of hardware during the surgical procedure. Thus, there remains a need for spinal fixation devices that facilitate simple and fast assembly of attachment of a spinal rod to a spine. It would be desirable to provide a device with pre-assembled components that will result in less time in assembling the components in the operating room.

SUMMARY OF THE INVENTION

In accordance with one or more embodiments of the present invention, a bone fixation assembly is provided comprising a fixation element having a head portion, a unitary coupling element having a first bore adapted to slidably receive the head portion of the fixation element, and a first locking element adapted to secure the head portion in the first bore. In certain embodiments, the coupling element has a second bore adapted to receive a spinal rod and a second locking element adapted to secure the spinal rod in the second bore.

According to one or more further aspects of the present invention, a bone fixation system assembly includes a fixation element having a substantially cylindrical head portion; a unitary coupling element having a first bore adapted to receive the head portion of the fixation element and to permit axial movement of the coupling element with respect to the fixation element, the coupling element having a second bore adapted to receive a spinal rod; a first locking element pre-assembled with the coupling member and adapted to secure the head portion in the first bore; and a second locking element pre-assembled with the coupling member and adapted to secure the spinal rod in the second bore.

According to one or more further aspects of the present invention, a bone fixation assembly includes: a fixation element having a head portion; a unitary coupling element having a first bore adapted to receive the head portion of the fixation element and to permit axial movement of the coupling element with respect to the fixation element; and a locking element including a ball ring and a locking nut adapted to exert radial force on the ball ring such that the ball ring exerts a compressive force on the head of the fixation element to secure the head of the screw in the coupling element.

According to still one or more further aspects of the present invention, a bone fixation assembly includes: a fixation element having a substantially cylindrical head portion; a unitary coupling element having a first bore adapted to receive the head portion of the fixation element and to permit axial, preferably polyaxial, movement of the coupling element with respect to the fixation element, and a first locking element including a locking nut that engages the first bore and a tapered opening adapted to allow polyaxial motion of the head of a fixation element inserted therethrough.

In still another embodiment of the invention, a method of fixing a bone in place is provided. The method comprises attaching a fixation element having a head portion to a bone, sliding a first bore of a unitary coupling element over the head portion, inserting a rod through a second bore of the coupling element, tightening a first locking element associated with the first bore to secure the head portion to the coupling element, and tightening a second locking element associated with the second bore.

According to one or more embodiments of the present invention, bone fixation assemblies are provided to connect spinal rods without any loose parts and very few steps (preferably only two steps) to lock the fixation element to the coupling member and the spinal rod to the coupling member. The assemblies of the present invention do not require any additional locking mechanism, and they reduce the assembly of small pieces of hardware during the surgical procedure.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS

Before describing several exemplary embodiments of the invention, it is to be understood that the invention is not limited to the details of construction or process steps set forth in the following description. The invention is capable of other embodiments and of being practiced or carried out in various ways.

Figure 1:
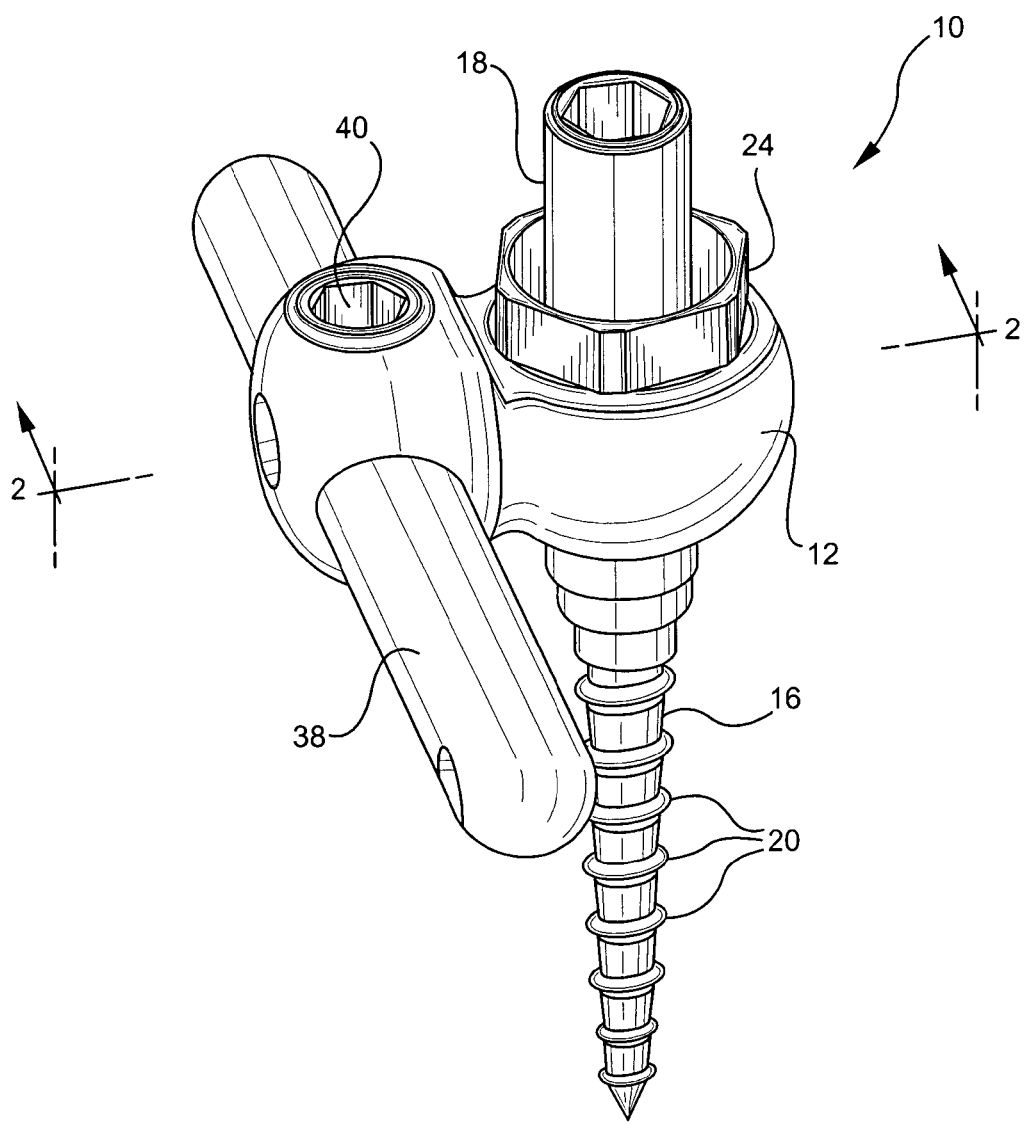
FIG. 1 is a partial perspective view of a bone fixation assembly with a spine rod secured thereto according to one or more embodiments of the present invention.
Figure 2:
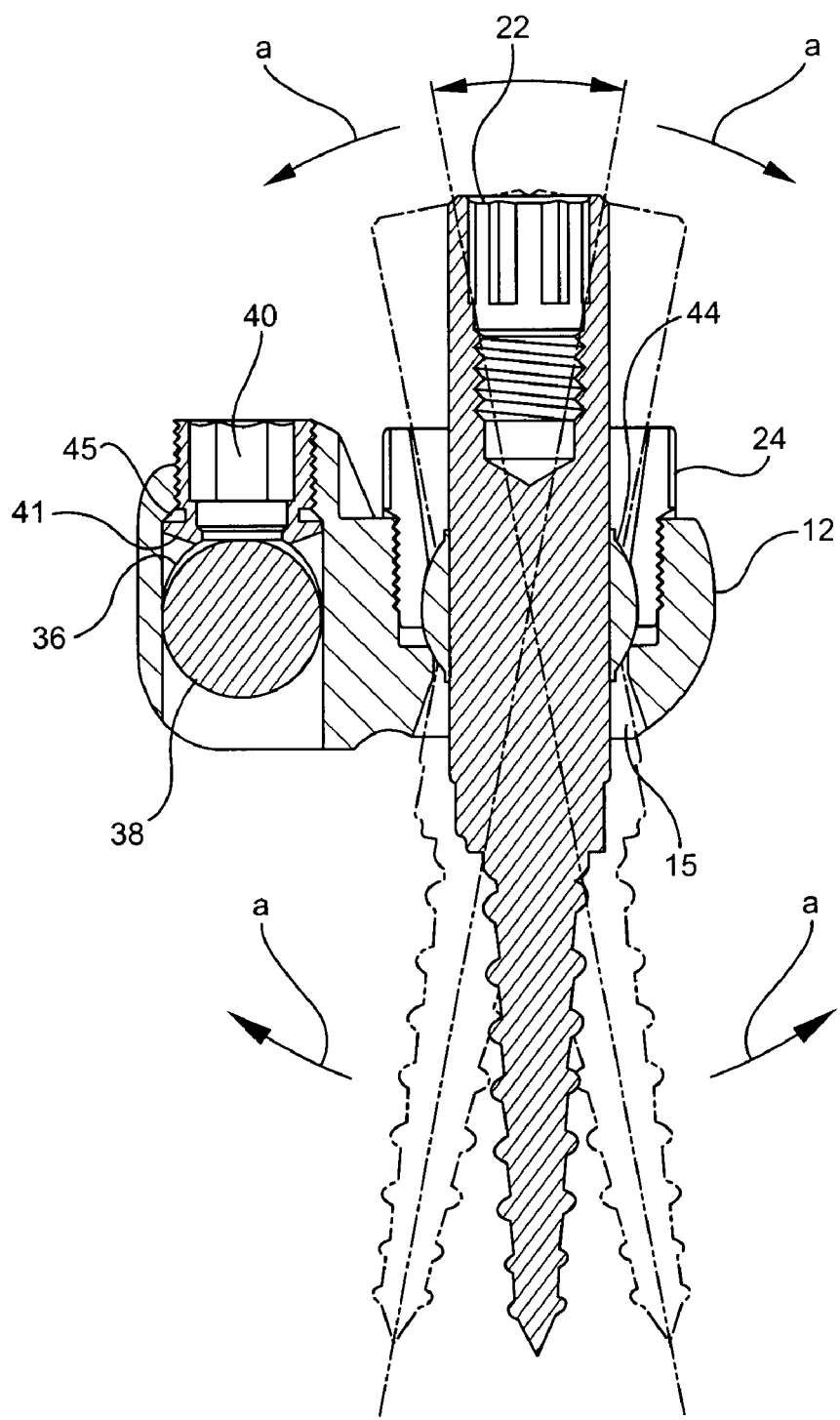
FIG. 2 is a cross-sectional view taken along line 2-2 of FIG. 1.
Figure 3:
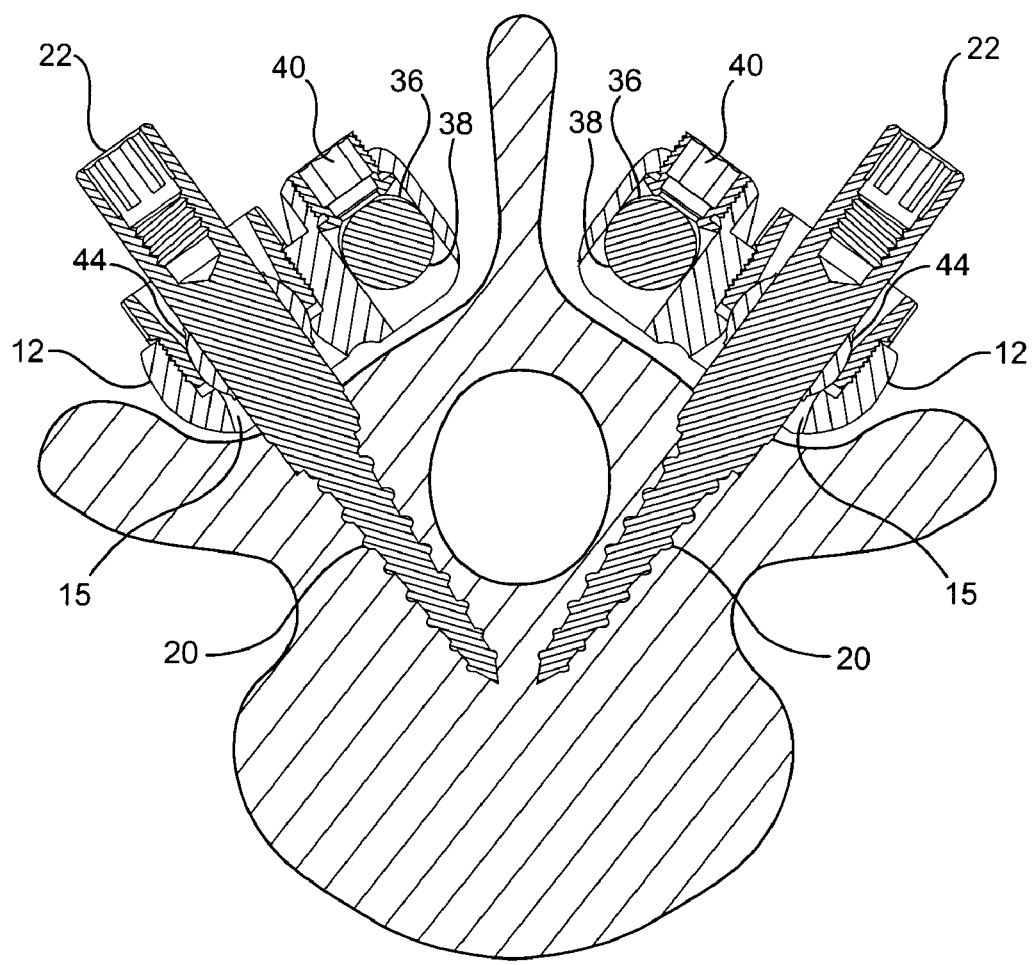
FIG. 3 is a sectional view of a bone fixation assembly with a spine rod and screw illustrating the manner in which the assembly is connected with a vertebra.

Referring now to the drawings and particularly to FIGS. 1-3, a bone fixation assembly 10, in accordance with certain preferred embodiments of the present invention, is shown. The bone fixation assembly may be secured to the pedicles 11 of vertebral bodies of a spinal column, as shown in FIG. 3. The fixation assembly includes a coupling element 12, preferably made of a biologically inert material, for example, any metal customarily used for surgical devices and particularly those used for bone screws and pins, such as titanium or stainless steel. Other suitable materials for the coupling element include, but are not limited to, alloys, composite materials, ceramics or carbon fiber materials.

The fixation assembly 10 includes a fixation element 16 having a head portion 18. The head portion 18 is preferably cylindrical, and preferably has a smooth outer surface to facilitate sliding on or in connection with the head portion 18, as will be described below. The head portion 18 can be constructed in other ways or in connection with other components to facilitate sliding of the coupling element with respect to the fixation element 16. The fixation element 16 could be any suitable fixation element for attachment to a bone, for example, a hook or a screw. In preferred embodiments, the fixation element includes a screw fastener having the head portion 18 and a threaded portion 20, and the threads are adapted to be engaged in bone material. The end of the screw fastener opposite the head portion 18 has a tip for insertion into bone, and external screw threads 20 extend between the tip and the head portion 18. The screw threads 20 have an inner diameter and an outer diameter. The fixation element, including the screw threads 20 and head portion 18, are preferably made of a biologically inert material, such as titanium or stainless steel.

In the embodiment shown in FIGS. 1-3, one end of the head portion of the fixation element includes a tool engagement surface 22. In the embodiment shown, the tool engagement surface 22 is in the form of a hollow female hex head adapted to receive an end of a hexagonal driver for turning the fixation element. It will be understood, however, that other internal or external tool engagement surfaces 22, can be used according to the present invention.

Figure 4:
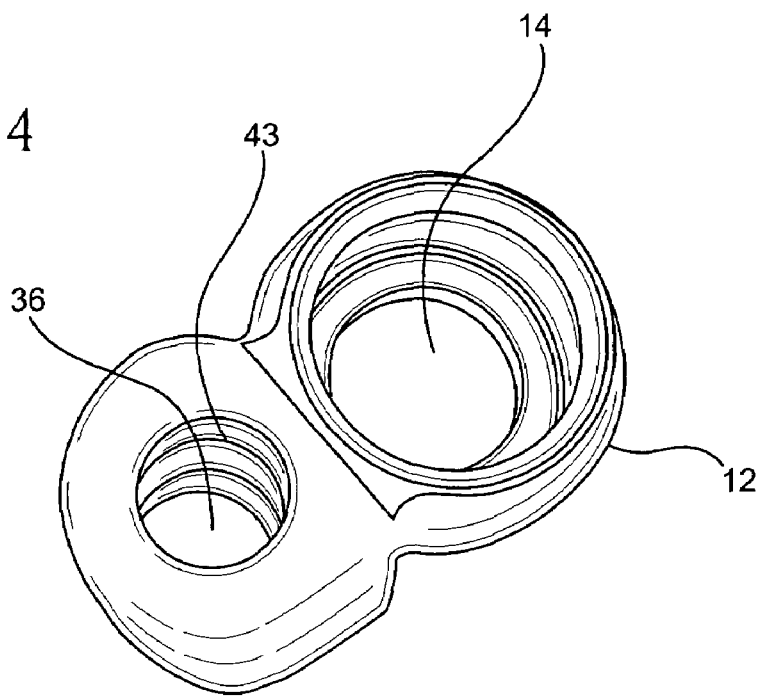
FIG. 4 is a top perspective view of a coupling element according to one or more embodiments of the present invention.

Coupling element 12, which is shown in more detail in FIG. 4, preferably comprises a unitary body and has at least a first bore 14 having a longitudinal axis adapted to receive the head portion 18 of the fixation element 16 and to permit axial, sliding movement of the coupling element 12 along the axis of the head portion 28 with respect to the fixation element. The fixation assembly further comprises a first locking element adapted to secure the head portion 18 in the first bore 14. According to one or more embodiments, the first locking element includes at least a locking nut 24.

Figure 7:
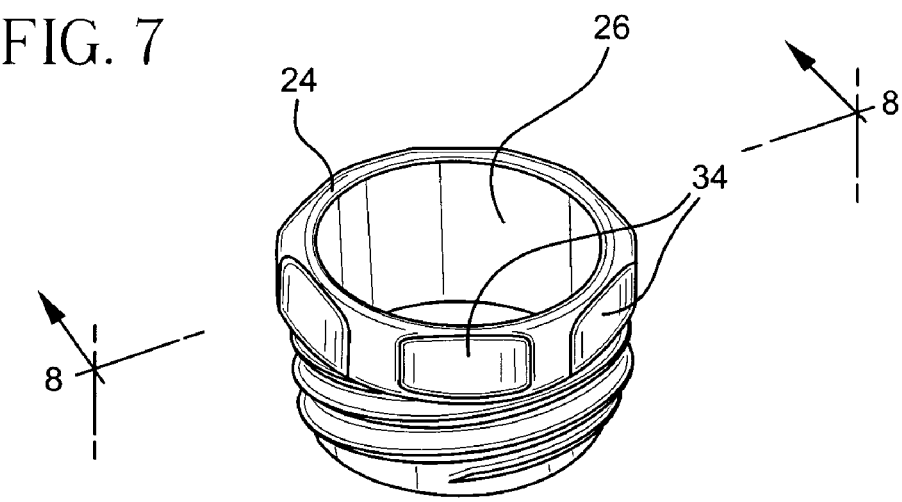
FIG. 7 is a perspective view of a locking nut for securing the head of a fixation element according to one or more embodiments of the invention.
Figure 8:
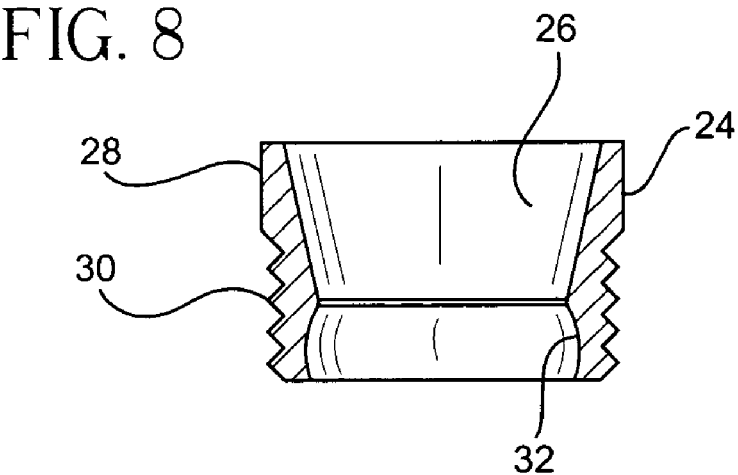
FIG. 8 is a cross-sectional view of the locking taken along line 8-8 in FIG. 7.

Further detail on the locking nut 24 is shown in FIGS. 7 and 8. Preferably, the locking nut 24 is hollow and has a bore 26 therethrough for receiving the head portion 18 of the fixation element 16. The locking nut 24 includes a receiving end 28, and the opening 26 at the receiving end 28 is flared or angled as shown in FIG. 8. The flared or tapered opening permits polyaxial motion of a fixation element inserted therethrough. In a preferred embodiment, the first bore 14 includes a bottom portion 15 that is tapered or flared in a direction opposite the taper or flared opening in the locking nut 24. The oppositely extended flared openings permit polyaxial movement between the fixation element and the coupling member. Preferably, the fixation element can move polyaxially as shown by the arrows "a" in FIG. 2. In preferred embodiments, the fixation element can move by at least 20 degrees polyaxially, as indicated by the arrows "a" in FIG. 2. The locking nut 24 further includes a seating end 30, and according to at least one embodiment, the seating end 30 includes an inner curved engagement surface 32 for engaging a ball ring, which will be described in more detail below. The ball ring, as seated in the inner curved engagement surface 32, facilitates polyaxial movement of the fixation element, and can do so in a controlled manner. The receiving end 28 of the locking nut may further include a plurality of flat surfaces 34 such that the receiving end 28 of the locking nut is hexagonally shaped and adapted to receive a wrench or other device adapted to turn the locking nut. According to certain preferred embodiments, the exterior surface of the receiving end 28 further includes male threads for engagement with complementary female threads on the interior of the first bore 14 of the coupling element 12.

Figure 5:
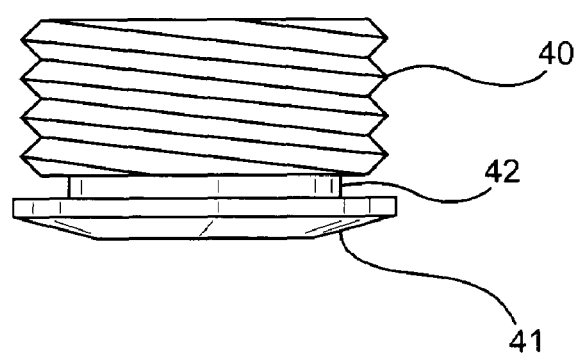
FIG. 5 is a side elevational view of a locking element for securing a spine rod to a bone fixation assembly according to one or more embodiments of the present invention.
Figure 6:
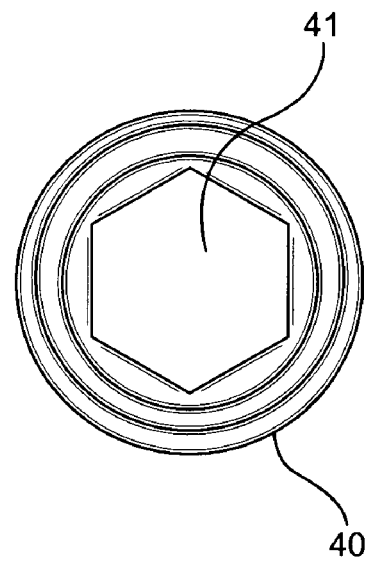
FIG. 6 is a top view of the locking element shown in FIG. 5.

According to one or more embodiments, the coupling element 12 includes a second bore 36 adapted provide an opening to receive a spinal rod 38 through the bore. The second bore 36 has a longitudinal axis that is substantially transverse to the longitudinal axis of the first bore 14. In these embodiments, a second locking element 40 is provided and is adapted to secure the spinal rod in the second bore. FIGS. 5 and 6 show additional details of the second locking element 40. The second locking element 40 is preferably in the form a set screw. The second locking element 40 includes a hexagonal shaped opening which is adapted to receive an end of a hexagonal driver for turning the second locking element 40. The second locking element 40 further preferably includes external threads 42 for engagement with complementary internal 43 threads on the surface of the second bore 36. The rod receiving opening and second locking element are thus adapted to capture and seat an orthopedic stabilizing rod therein. In preferred embodiments, both the first and second locking elements 22, 40 are permanently seated in the coupling element 12 such that the locking elements cannot be inadvertently removed from the coupling element. Inadvertent removal of the locking element 40 can be accomplished by providing a flared portion or lip 41 on the end of the locking element opposite the tool engagement surface. A shoulder 45 associated with the respective bore of the coupling element prevents removal of the locking element 40. The flared portion or lip 41 has a diameter that is greater than the threaded portion of the locking element 40. The shoulder 45 associated with the bore 36 provides an opening in the bore 36 that is greater than the diameter of the threaded portion of the locking element 40, but smaller than the diameter of the flared portion or lip 41 on the locking element 40. Thus, when the locking element is turned in a direction to back the locking element out of the bore 36, the shoulder 45 and flared portion or lip 41 prevent the locking element 40 from coming out of the bore 36. Although the shoulder 45 and flared portion or lip 41 are shown with respect to the second bore 36, it will be understood that such a structure can be used with respect to the first bore 14 to prevent inadvertent removal of the locking nut 24 from the first bore. It will be understood, of course, that other means and structures can be used to prevent inadvertent removal or pre-assembly of the locking element 40 and locking nut 24 in their respective bores. For example, the locking element and/or locking nut could be press fit into the bores and friction locked to prevent inadvertent removal. Alternatively, detents on the surfaces of the bores or the locking nut and locking element could be utilized to prevent inadvertent removal of the locking element or locking nut.

Figure 9:
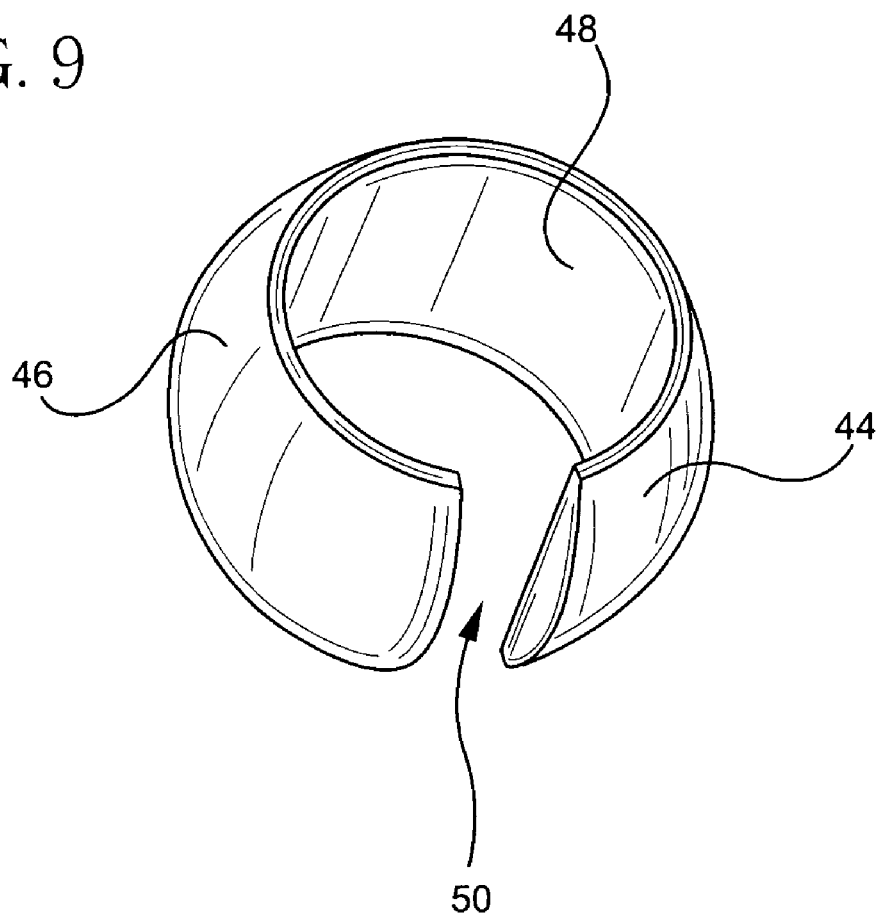
FIG. 9 is a perspective view of a ball ring according to one or more embodiments of the present invention.

According to preferred embodiments of the invention, the first locking element comprises a locking nut 24 that cooperates with a ball ring 44 to lock the head portion 18 of the fixation element to the coupling member 14. As shown in FIG. 2, the ball ring 44 is seated within the first bore 14 and at least a portion of the locking nut 24 circumferentially surrounds a portion of the ball ring. In preferred embodiments, the ball ring 44 is pre-assembled and permanently seated in the first bore of the coupling member. In preferred embodiments, the curved engagement surface of the locking nut 24 engages the exterior surface 46 of the ball ring 44. FIG. 9 shows a detailed view of the ball ring. The ball ring 44 shown in FIG. 9 comprises a generally spherical outer surface having an opening 48 through the body coaxial with the first bore and adapted to receive the head portion 18 of the fixation element 16. As shown in FIG. 9, the ball ring 44 includes a gap 50 in the outer surface, allowing the ball ring 44 to be compressed such that the inner diameter of the ball ring opening 48 is reduced when the ball ring is compressed. The ball ring 44 and the gap 50 are designed such that when the ball ring 44 is compressed, the diameter of the opening 48 is less than the diameter of the head portion 18 of the screw so that the head portion of the screw is securely and snugly held in place. Compression of the ball ring occurs when the locking nut 24 is tightened. Engagement of the male threads of the locking nut with the female threads in the first bore cause the engagement surface 32 of the locking nut to engage the outer surface 46 of the ball ring 44, causing the ball ring to compress onto the head portion 18 of the screw. This compression exerts a radial force on the exterior surface of the ball ring 44. It is to be understood that the ball ring 44 may be configured differently than shown in FIG. 9. For example, instead of a single gap 50 in the outer surface of the ring, the ring may include a plurality of split openings that do not extend through the entire exterior surface of the split ring.

Additionally, while the foregoing preferred structures facilitate axial movement of the coupling element, other structures are also available for this purpose. For example, a split collet could surround a spherical head portion and the outer surface of the collet could cooperate with the coupling element or other components to permit axial sliding before being compressed around the spherical head portion. Of course, in such a construction, the extent of axial sliding may be limited by the size of the coupling element, whereas in the preferred embodiment, the extent of sliding may be limited by the length of the head portion of the fixation element.

According to a preferred embodiment, a fixation assembly 10 is provided in a package including the coupling element 12 having the set screw 40, locking nut 24 and ball ring 44 permanently pre-seated in the coupling element 12 to reduce the number of loose parts and prevent any small loose parts from being lost, or from having to be handled and manipulated during surgery, the ball ring 44 is generally kept in the interior of the coupling element by virtue of the nut 24 being captured in connection with the coupling element. As used herein, the terminology "permanently pre-seated" means that the elements are prevented from being inadvertently removed from their respective bores, as opposed to being loose in a package and requiring assembly of the individual components. Such a pre-seated construction helps to prevent the surgeon from losing or dropping small loose parts during preparation for a surgical procedure.

In use, the components are removed from the package, and a fixation element such as a screw 16 having a generally smooth, cylindrical head portion 18 is inserted into the first bore 14 of the coupling element and through the coaxial openings in the ball ring 44 and locking nut 24. A spinal rod 38 is inserted in the second bore of the coupling member. The set screw 40 may be tightened to exert force on the spinal rod and lock the spinal rod in place. The fixation element 16 may then be inserted into a bone, preferably into a previously drilled pilot hole in the bone. The fixation element is then preferably screwed into the bone using a driver or other appropriate device, advancing the fixation element along its longitudinal axis into the bone. Prior to tightening the locking nut 24, the angle of the fixation element is adjusted by moving it in the tapered opening 26 in the locking nut and the oppositely tapered opening of the first bore 14. Due to the opposite taper of the first bore 14 of the coupling element and the taper of the opening in the locking nut 24, the fixation assembly can be manipulated to cover a broader range of angles for capturing an orthopedic stabilizing rod. The range of angles that can be covered is 20 degrees polyaxially about the head portion 18 of the fixation element. After the proper angulation is determined, the locking nut is tightened, exerting a compressive radial force on the ball ring and locking the head portion of the fixation element in place. Preferably, the connector is locked in the manner described above in two steps. However, according to certain procedures, the locking nut may be tightened on the head portion of the fixation element first, and then the set screw may be tightened on the spinal rod after the locking nut has been tightened. Achieving sufficient angulation between anchoring elements while engaging the orthopedic rod is essential for assemblies mounted in spines having abnormal curvatures. Sufficient angulation is also important in the cervicothoracic junction of the spine.

Although the invention herein has been described with reference to particular embodiments, it is to be understood that these embodiments are merely illustrative of the principles and applications of the present invention. For example, the bores for receiving the spinal rods or heads of the fixation elements may have non-circular cross-sectional shapes, such as square, pentagonal, elliptical, etc. It is therefore to be understood that numerous modifications may be made to the illustrative embodiments and that other arrangements may be devised without departing from the spirit and scope of the present invention as defined by the appended claims and their equivalents.

The invention claimed is:

1. A bone fixation assembly comprising:
a unitary coupling element having a first bore having an axis, the first bore adapted to receive a head portion of a fixation element and to permit axial, sliding movement of the coupling element relative to the fixation element, the coupling element having a second bore adapted to receive a spinal rod;
a first locking element adapted to secure the head portion of the fixation element in the first bore at any point along the length of the head portion of the fixation element, wherein the first locking element comprises a compressible ball ring; and
a second locking element adapted to secure the spinal rod in the second bore.

2. The bone fixation assembly of claim 1, wherein the first locking element further comprises a locking nut.

3. The bone fixation assembly of claim 2, wherein the locking nut contains external male threads that engage female threads formed in the first bore.

4. The bone fixation assembly of claim 3, wherein the compressible ball ring is seated within the first bore and at least a portion of the locking nut circumferentially surrounds a portion of the ball ring.

5. The bone fixation assembly of claim 4, wherein engagement of the male threads of the locking nut with the female threads in the first bore exerts radial force on the compressible ball ring to secure the head of the fixation element in the first bore.

6. The bone fixation assembly of claim 5, wherein the locking nut is in a locked position, and the compressible ball ring is in contact with the coupling member and the locking nut.

7. The bone fixation assembly of claim 6, wherein the second locking element includes a set screw.

8. The bone fixation assembly of claim 7, wherein the set screw is permanently seated in the coupling member.

9. The bone fixation assembly of claim 8, wherein the locking nut and compressible ball ring are permanently seated in the first bore.

10. The bone fixation assembly of claim 8, wherein the locking nut cannot be removed from said coupling element after connection therewith.

11. The bone fixation assembly of claim 10, wherein a portion of the first bore is tapered and the locking nut includes a tapered opening to permit polyaxial motion between the fixation element and the connector.

12. The bone fixation assembly of claim 11, wherein the taper in the first bore and the taper in the locking nut extend in opposite directions.

13. The bone fixation assembly of claim 12, wherein the fixation element includes a screw.

14. The bone fixation assembly of claim 1, wherein the compressible ball ring is at least partially split.

15. The bone fixation assembly of claim 1, wherein said second bore has an axis transverse to the axis of the first bore.

16. The bone fixation assembly of claim 1, wherein said second locking element is connected to said coupling element and cannot be removed from said coupling element after connection therewith.

17. The bone fixation assembly of claim 16, wherein second locking element includes a flared lip that cooperates with a shoulder associated with the coupling element to prevent inadvertent removal of the second locking element.

18. The bone fixation assembly of claim 1, wherein the first locking element is connected to said coupling element and cannot be removed from said coupling element after connection therewith.

19. The bone fixation assembly of claim 1, further comprising a fixation element having a head portion, wherein the head portion of the fixation element is inserted in the first bore.

20. A bone fixation assembly comprising:
a unitary coupling element having a first bore adapted to slidingly receive a head portion of a fixation element, and a second bore adapted to receive a spinal rod;
a first locking element pre-assembled with the coupling element and adapted to secure the head portion of the fixation element in the first bore at any point along the length of the head portion of the fixation element, the first locking element including a compressible ball ring; and
a second locking element pre-assembled with the coupling element and adapted to secure the spinal rod in the second bore.

21. The bone fixation assembly of claim 20, wherein the first bore permits axial movement of the coupling element relative to the fixation element.

22. The bone fixation assembly of claim 21, wherein the first bore permits polyaxial movement of the coupling element relative to the fixation element.

23. The bone fixation assembly of claim 22, wherein the first bore has an axis, and the second bore has an axis transverse to the first bore.

24. The bone fixation assembly of claim 21, wherein the locking nut is adapted to exert radial force on the ball ring.

25. The bone fixation assembly of claim 20, wherein the compressible ball ring is seated in the first bore and cooperates with a locking nut threaded in the first bore.

26. The bone fixation assembly of claim 20, further comprising a fixation element having a head portion, wherein the head portion of the fixation element is inserted in the first bore.

27. The bone fixation assembly of claim 20, wherein said compressible ball ring is at least partially split.

28. A bone fixation assembly comprising:
a unitary coupling element having a first bore adapted to slidingly receive a head portion of a fixation element and to permit axial movement of the coupling element relative to the fixation element; and
a locking element including a ball ring and a locking nut associated with the head portion of the fixation element to exert a radial force on the ball ring such that the ball ring exerts a compressive force on the head portion of the fixation element to secure the head portion of the fixation element in the coupling element at any point along the length of the head of the fixation element.

29. The bone fixation assembly of claim 28, further comprising a fixation element having a head portion, wherein the head portion of the fixation element is inserted in the first bore.

30. The bone fixation assembly of claim 28, wherein said ball ring is at least partially split.

31. A bone fixation assembly comprising:
a unitary coupling element having a first bore adapted to slidingly receive a head portion of a fixation element and to permit axial movement of the coupling element relative to the fixation element;
a compressible ball ring seated in the first bore adapted to secure the head of the fixation element to the coupling element when the ball ring is compressed at any point along the length of the head of the fixation element; and
means for exerting compressive radial force on the ball ring.

32. The bone fixation assembly of claim 31, wherein the means for exerting compressive radial force includes a locking nut.

33. The bone fixation assembly of claim 32, wherein the locking nut contains external male threads adapted to engage internal female threads in the first bore.

34. The bone fixation assembly of claim 31, further comprising a fixation element having a head portion, wherein the head portion of the fixation element is inserted in the first bore.

35. The bone fixation assembly of claim 31, wherein the compressible ball ring is at least partially split.

36. A bone fixation assembly comprising:
a unitary coupling element having a first bore adapted to slidingly receive a head portion of a fixation element and to permit axial movement of the coupling element relative to the fixation element; and
a first locking element including a locking nut that engages the first bore and a tapered opening adapted to allow polyaxial motion of the head portion of the fixation element inserted therethrough, the first locking mechanism further including a compressible ball ring for locking the head portion of the fixation element at any position along its length.

37. The bone fixation assembly of claim 36, wherein the locking nut cooperates with the compressible ball ring to exert force on the head of the fixation element to lock the fixation element with respect to the coupling element.

38. The bone fixation assembly of claim 36, wherein the compressible ball ring is at least partially split.

39. A bone fixation assembly comprising:
a fixation element having a substantially cylindrical, smooth head portion;
a unitary coupling element having a first bore adapted to slidingly receive the head portion of the fixation element and to permit axial, sliding movement of the coupling element relative to the fixation element, the coupling element having a second bore adapted to receive a spinal rod;
a first locking element including an externally threaded locking nut adapted to cooperate with threads in the first bore and exert radial compressive force on a compressible ball ring slidably mounted on the head portion of the fixation element pre-seated in the first bore to secure the head portion of the fixation element in the first bore at any point along the length of the head portion of the fixation element, the locking nut permitting polyaxial motion of the fixation element; and
a second locking element pre-assembled with the coupling member and adapted to secure the spinal rod in the second bore.

40. The bone fixation assembly of claim 39, wherein the compressible ball ring is at least partially split.

* * * * *

UNITED STATES PATENT AND TRADEMARK OFFICE
CERTIFICATE OF CORRECTION

| | | |
|---|---|---|
| PATENT NO. | : 7,648,522 B2 | Page 1 of 1 |
| APPLICATION NO. | : 10/695849 | |
| DATED | : January 19, 2010 | |
| INVENTOR(S) | : Jérôme David | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 550 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,648,522 B2
APPLICATION NO. : 10/695849
DATED : January 19, 2010
INVENTOR(S) : Jérôme David et al.

Page 1 of 1

It is certified that error appears in the above-identified patent and that said Letters Patent is hereby corrected as shown below:

Col. 3, Line 17, insert --nut-- after "view of the locking"
Col. 4, Line 2, delete "," after "surfaces 22"
Col. 4, Line 14, replace "detail" with --details--
Col. 4, Line 14, replace "is" with --are--
Col. 4, Line 45, insert --to-- after "adapted"
Col. 4, Line 52, insert --of-- after "in the form"
Col. 4, Line 53, insert -- - -- between "hexagonal shaped"
Col. 5, Line 21, insert -- - -- between "friction locked"
Col. 5, Line 50, replace "cause" with --causes--
Col. 7, Line 64, insert --said-- after "wherein"

Signed and Sealed this
First Day of March, 2011

David J. Kappos
*Director of the United States Patent and Trademark Office*